United States Patent
Milton et al.

(10) Patent No.: US 11,357,535 B2
(45) Date of Patent: Jun. 14, 2022

(54) SCALPEL WITH RETRACTABLE BLADE

(71) Applicant: Trevor John Milton, Somerset West (ZA)

(72) Inventors: Trevor John Milton, Somerset West (ZA); Norman Anthony Nieuwenhuizen, Boksburg (ZA)

(73) Assignee: Trevor John Milton, Somerset West (ZA)

( * ) Notice: Subject to any disclaimer, the term of this patent is extended or adjusted under 35 U.S.C. 154(b) by 106 days.

(21) Appl. No.: 16/489,997

(22) PCT Filed: Mar. 9, 2018

(86) PCT No.: PCT/IB2018/051537
§ 371 (c)(1),
(2) Date: Aug. 29, 2019

(87) PCT Pub. No.: WO2018/163112
PCT Pub. Date: Sep. 13, 2018

(65) Prior Publication Data
US 2020/0121348 A1    Apr. 23, 2020

(30) Foreign Application Priority Data
Mar. 10, 2017 (GB) ..................... 1703887

(51) Int. Cl.
*A61B 17/3211* (2006.01)
(52) U.S. Cl.
CPC . *A61B 17/3211* (2013.01); *A61B 2017/32113* (2013.01)
(58) Field of Classification Search
CPC ...... A61B 17/3211; A61B 2017/32113; B26B 5/001; B26B 5/003; B26B 5/005;
(Continued)

(56) References Cited

U.S. PATENT DOCUMENTS

| 4,621,425 A * | 11/1986 | Stoutenberg ............ B26B 5/001 |
| | | 30/162 |
| 6,254,621 B1 * | 7/2001 | Shackelford ....... A61B 17/3213 |
| | | 30/162 |
| 2004/0158269 A1 * | 8/2004 | Holman ............. A61B 17/3217 |
| | | 606/167 |

FOREIGN PATENT DOCUMENTS

| EP | 2732780 A1 | 5/2014 |
| WO | WO 2006044865 A2 | 4/2006 |
| WO | WO 2015134601 A1 | 9/2015 |

OTHER PUBLICATIONS

International Search Report and Written Opinion dated Jun. 13, 2018 in International Application No. PCT/IB2018/051537, in 8 pages.

* cited by examiner

*Primary Examiner* — Kathleen S Holwerda
*Assistant Examiner* — Lauren Dubose
(74) *Attorney, Agent, or Firm* — Knobbe, Martens, Olson & Bear, LLP

(57) ABSTRACT

A scalpel has a handle (1) and a blade carrier (2) movable within a longitudinally extending cavity therein between an operative position in which a blade (5) on the blade carrier is exposed for use and an inoperative retracted position. A manually operable slider (4) moves the blade carrier (2) that has a catch face (21) directed rearwards in the operative position. The catch face partially aligns with a stop face (22) provided on the handle (1) in the normal operative position of the blade carrier such that force exerted on a blade carried by the blade carrier in the direction of the length of the handle causes engagement of the catch face with the stop face to arrest movement of the blade carrier into the cavity. Transverse biasing of the blade carrier (2) is overcome by pressure exerted on the slider (4) to retract the blade carrier (Continued)

(2) into the handle with the catch face (21) passing the stop face (22).

13 Claims, 3 Drawing Sheets

(58) Field of Classification Search
CPC ......... B26B 5/006; B26B 9/02; B26B 27/005;
B26B 1/08
USPC ....................................................... 606/167
See application file for complete search history.

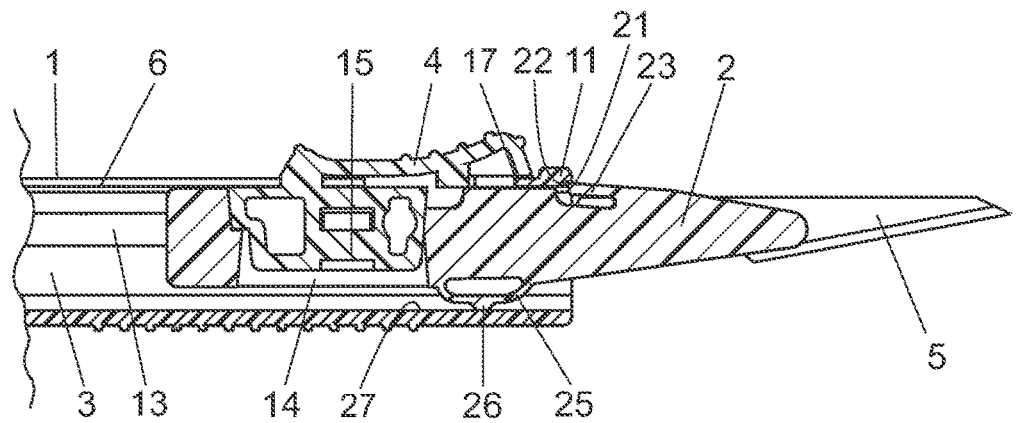
Figure 7
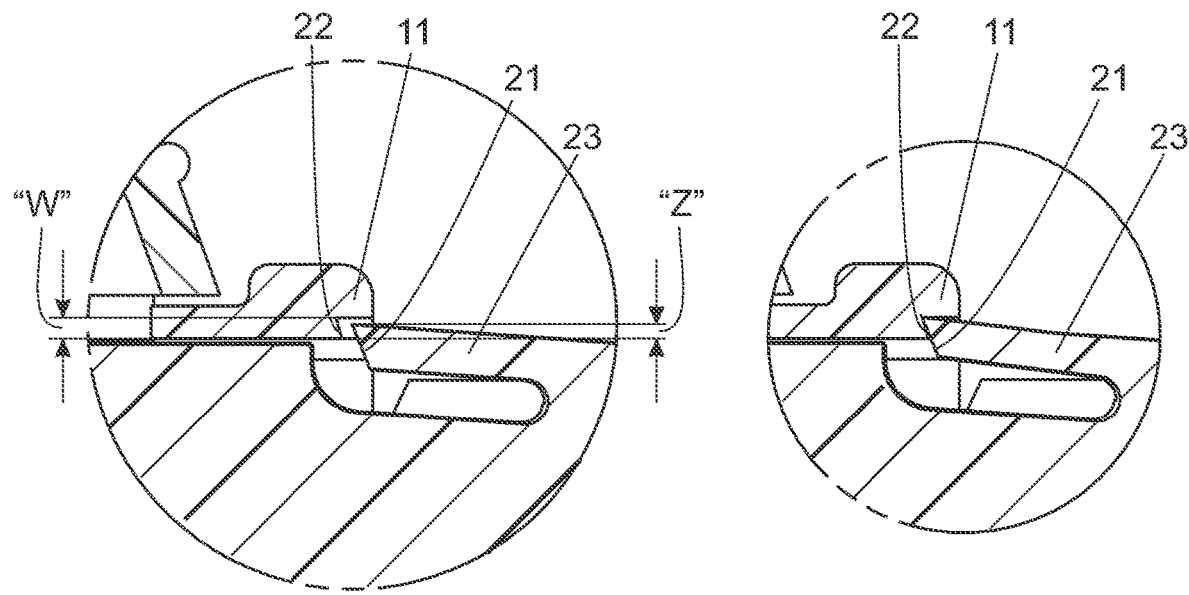
Figure 8
Figure 9

SCALPEL WITH RETRACTABLE BLADE

CROSS-REFERENCE TO RELATED APPLICATION

This application is a U.S. National Phase of International Application No. PCT/IB2018/051537, filed Mar. 9, 2018, which claims priority from United Kingdom patent application number 1703887.8 filed on Mar. 10, 2017, each of which is incorporated by reference herein.

FIELD OF THE INVENTION

This invention relates to a scalpel having a retractable blade, typically, but not necessarily, a disposable scalpel. More particularly, the invention relates to a scalpel in which movement of a blade relative to a supporting scalpel handle between an extended operative position and a retracted inoperative position is achieved by moving a blade carrier by way of a thumb operable slider attached, generally by way of a slot through a wall of the handle, to the blade carrier that is slideable within the handle.

BACKGROUND TO THE INVENTION

Disposable scalpels having retractable blades have been produced in many different forms in one of which a slider projects through a slot in one edge of a handle that can be considered to be a top edge of the scalpel handle having a cavity into which a blade can be retracted from an exposed operative position. The design of a type of scalpel that applicant prefers, as well as its background and the motivation for its development, are described in published international patent application number WO2004/045428 the content of which is incorporated herein by reference.

There are a number of factors that are considered to be desirable as regards scalpels with retractable blades and that are present to some extent in existing scalpels, these being factors that contribute to the scalpel blade being held firmly in its operative position; being held positively in its retracted inoperative position; and also a preferred facility aimed at preventing re-use of a scalpel by providing a final irreversible retracted position.

In one of applicant's current designs, the blade carrier with its attached blade and externally accessible slider that clips into the blade carrier by way of a slot in the top of the handle is movable into a fully forward operative position by moving the slider to its fully forward position. In that position, the slider contacts a closed forward end of the slot thus preventing further forward movement. When this position is reached it is accompanied by an audible "click" that signifies the full extent of travel. The "click" is created by a trapezoidal tooth formation on a side of the slider that urges a co-operating tooth formation on the handle slot laterally outwards followed by the co-operating tooth formation snapping back into cooperation with the formation on the slider thus producing the audible "click".

In the fully forward position, the slider tooth formation is forward of the cooperating handle tooth formation and the handle resilience thus provides a restraining force against rearward movement of the blade carrier with blade and slider. With normal use of the scalpel unit, the slider may be held by the forefinger or between the forefinger and thumb, depending on user preference, or of necessity, as dictated by the procedure. This holding technique provides an additional restraining force for the blade against rearward movement.

However, certain procedures may preclude holding of the slider and in such instances blade restraint is dependent only on the interaction of the cooperating trapezoidal tooth formations and the handle resilience. In the instance of performing certain types of operations such as a stabbing movement or the like, there is a chance that the blade will be forced rearwards into the handle with the trapezoidal formations being forced to disengage and such an occurrence could be deleterious.

Applicant perceives a need for scalpel having a retractable blade in which this possibility is obviated, at least to a substantial extent. It is, however, important that no additional or uncommon actions be required of a surgeon in order to activate or deactivate any additional lock or restraining feature.

EP 2732780 A1 discloses a scalpel having a blade carried on a blade carrier and which may be extended from a handle by side mounted sliders. A latching element or spring pawl on the blade carrier engages with an abutment on the handle when the blade is fully extended to prevent the blade from retracting under an axial rearward force. The spring pawl must deflect down, hence away from abutment, in order for blade carrier to retract. Slider left and right halves clip together, onto the blade carrier, but are not rigidly attached to blade carrier. The slider halves are permitted to slide axially a short distance relative to blade carrier. A tab feature with end inclined ramp face is integral with each slider half. In the forward lock position, the inclined ramp face of the tab feature is in close proximity to the naturally positioned inclined face of spring pawl. When one or other slider half is moved rearwards under finger movement, the tab feature moves rearward and contacts with the stationary spring pawl causing it to hinge downwards and in so doing causing the free end of spring pawl to disengage from abutment face. Once the spring pawl is disengaged from the abutment the slider halves are prevented from further independent axial movement relative to blade carrier. Further rearward movement of slider halves causes the blade carrier to slide rearwards in cooperation with slider halves and withdraw the blade into the handle. The positioning of the slider halves on each side of the handle requires of the user an unnatural movement in that the user will tend to grasp the slider halves between thumb and forefinger and then drawing back while gripping the handle with the remaining fingers. Furthermore, the spring pawl is constantly under tension when in the retracted position which can lead to weakening or deformation thereof. Similarly, the action of the tab feature on the spring pawl to cause disengagement from the abutment face can also cause weakening or deformation of the spring pawl with repeated extension and retraction of the blade and blade carrier.

A further potential difficulty with the scalpel disclosed in this document is that the forward lock could conceivably be deactivated by inadvertently pulling back on the slider while performing a stabbing action. This is a foreseeable result of gripping the sliders between the forefinger and thumb while pushing forward against resistance using the remaining fingers and palm.

WO 2015/134601 A1 discloses a scalpel having a blade carried on a blade carrier and which may be extended from a handle by a pusher or slider located in a recess in the blade carrier. A latching element or pawl on the blade carrier engages within a lock member or port in the handle when the blade is fully extended to prevent the blade from retracting under an axial rearward force. The pawl is biased to this position by a leaf spring under the slide. The latching element may be disengaged by pressing the slider down against the bias of the spring. This requires an unnatural finger movement as the slider must be pressed down against the bias of the spring with a forward movement while at the same time dragging in a rearwards direction.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided a scalpel having a handle with a longitudinally extending cavity therein, a blade carrier within the cavity and movable longitudinally relative to the handle between an operative position in which a blade carried by the blade carrier is exposed for use at an open end of the cavity and an inoperative position in which a blade carried thereby is retracted within the cavity in the handle, and a manually operable slider associated with the blade carrier and passing through a slot in a wall of the handle at a top edge thereof, wherein the blade carrier is confined to longitudinal movement within the cavity by longitudinally extending co-operating guide surfaces, the scalpel being characterized in that the blade carrier or slider has a catch face directed rearwards in the operative position with the catch face being in at least partial co-operating alignment with a co-operating stop face provided on the handle in the normal operative position of the blade carrier such that force exerted on a blade carried by the blade carrier in a direction corresponding to a length of the handle causes engagement of the catch face with the stop face to arrest movement of the blade carrier into the cavity in the handle, and in that the co-operating guide surfaces are configured to allow limited transverse movement of the guide surfaces relative to each other and are biased to a position in which the catch face is in said at least partial co-operating alignment with the co-operating stop face provided on the handle with the biasing being configured to be overcome by pressure exerted on the slider that corresponds to pressure required to retract the blade carrier into the handle so that the catch face and stop face can pass each other during a retraction of the blade into the handle consequent on transverse movement of the guide surfaces relative to each other.

Further features of the invention provide for the catch face to be defined by an end face of an integral resiliently flexible cantilever pawl formation located on a top of the blade carrier and extending rearwards with the catch face transverse to the handle and being inclined upwards and rearwards towards a rear edge thereof in which instance the stop face is shaped complimentarily and is arranged to cause the cantilever pawl formation to flex upwards to promote full engagement of the two faces in instances in which partial alignment is present; for the stop face to be formed in an integral bridge at the front end of the top edge where the handle has an endless open end to the cavity; for the longitudinally extending co-operating guide surfaces to include at least one, and preferably two opposite longitudinally extending guide keys or grooves on the blade carrier co-operating with one or two longitudinally extending grooves or keys on one or both inner surfaces of the cavity such that the keys and grooves guide the blade carrier for longitudinal movement along the handle in which instance the grooves are slightly wider than the keys to provide for movement of the blade carrier away from the top of the handle to enable the catch face to pass the stop face during retraction of the blade into the handle by pressure on the slider; and for the biasing of the blade carrier towards the top of the handle to be achieved by a leaf spring formation integral with the blade carrier and preferably in the form of a squat closed loop at an edge of the blade carrier remote from the catch face with the leaf spring formation or a skid carried thereby sliding on a surface of the cavity remote from the stop face.

The depth of the stop face will generally depend on the physical properties of the plastic being used for the handle and whilst the catch face may be in total longitudinal alignment with the stop face it is presently considered to be more appropriate to provide a partial co-operating alignment with the catch face being laterally movable to create full engagement with the stop face by virtue of it being formed at an end of a somewhat flexible cantilever pawl. Typically, the depth of the stop face in a direction transverse to the co-operating guide surfaces could conveniently range between 0.1 and 0.7 millimetres and preferably between 0.5 and 0.6 millimetres.

The extent of a partial co-operating longitudinal alignment of the catch face with the co-operating stop face provided on the handle could generally be within the range of 0.1 to 0.6 millimetres and preferably from 0.3 to 0.5 millimetres transverse to the length of the handle.

In order to ensure proper movement of the catch face into full or partial alignment with the stop face, the normal terminal position of the blade carrier is such that the stop face and catch face are separated by a distance of between 0.1 and 0.6 millimetres and preferably between 0.2 and 0.5 millimetres. The arrangement is preferably such that a surgeon using the scalpel would not notice the additional movement of the blade carrier relative to the handle when the blade carrier moves to cause engagement of the catch face with the stop face.

The biasing of the blade carrier is configured to be overcome by normal pressure exerted on the slider that would correspond to that required to retract the blade carrier into the handle in a conventional routine manner.

The movement of the blade carrier transverse to the guide surfaces is selected to ensure a clear passage of the catch face past the stop face when the blade carrier is retracted by normal operation of the slider and the extent of that movement could be in the range of between 0.3 and 0.6 millimetres, preferably 0.5 millimetres, in instances in which partial co-operating longitudinal alignment of the catch face with the co-operating stop face is provided and is from 0.3 to 0.5 millimetres.

The handle is preferably moulded as a single piece moulding with an integral bridge defining an endless open end to the cavity through which the blade carrier may be introduced into the cavity. A separately formed slider snap fits to the blade carrier after introduction thereof through the open end of the cavity to form a blade carrier and slider assembly with a part of the slider passing through a slot along the top of the handle.

In order that the above and other features of the invention may be more fully understood one embodiment thereof will now be described with reference to the accompanying drawings.

BRIEF DESCRIPTION OF THE DRAWINGS

In the drawings:—

FIG. 7 is a sectional elevation taken along line VI to VI in FIG. 3;

FIG. 8 is a very much enlarged side detail showing the catch face and stop face in their disengaged positions in which insufficient force is exerted on the blade to cause movement of the blade carrier into the handle by a very small distance; and, FIG. 9 is the same as FIG. 8 but shows the catch face moved into co-operative engagement with the stop face and the cantilever pawl somewhat flexed.

DETAILED DESCRIPTION WITH REFERENCE TO THE DRAWINGS

Figure 1:
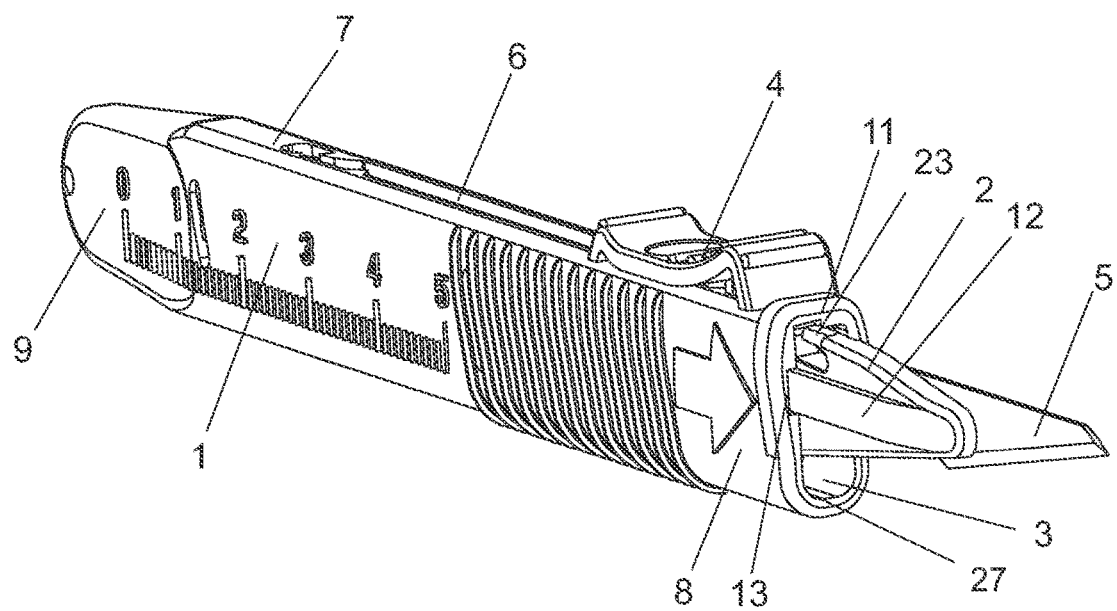
FIG. 1 is a three dimensional view from the front region of a scalpel according to the invention but offset such that the top edge of the handle is somewhat visible with a scalpel blade in its outermost operative position.

In the embodiment of the invention illustrated in the drawings, a scalpel comprises a single piece injection moulded plastics handle (1), and a blade carrier (2) slideable in a longitudinal cavity (3) within the plastics handle. A separately moulded, manually operable slider (4) that combines with the blade carrier to which a scalpel blade (5) is fitted for use, forms a blade carrier assembly.

The handle has a longitudinally extending slot (6) communicating with the cavity and extending in the wall along its operatively top edge (7) from a forward end (8) of the handle towards a rear end (9) thereof. An integral bridge (11) at the front end of the handle forms a top edge to an endless open end to the cavity and provides dimensional stability to the front end for firmly holding the blade carrier in its extended operative position.

Figure 6:
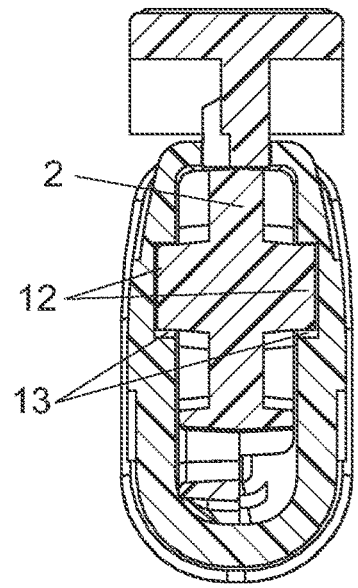
FIG. 6 is a cross-section taken along line V to V in FIG. 2.

The blade carrier is elongate and has a longitudinally extending key (12) on each side thereof that is received in a cooperating groove (13) (see especially FIG. 6) in each side wall of the cavity, these operatively forming longitudinally extending co-operating guide surfaces. The blade carrier is configured to slide longitudinally within the cavity and to receive and support a variety of different scalpel blade types. Clearly the blade carrier is shaped in cross-section to be introduced through the open end of the cavity.

The blade carrier has a socket (14) configured to receive an integral tongue (15) extending from the slider, the tongue having a retainer formation that locks onto the blade carrier in irreversible manner when the tongue is introduced into the socket by way of the slot with the blade carrier in the cavity. The blade carrier is thus held captive within the cavity and can be slid forwards and rearwards by manually operating the slider, generally by a person holding the scalpel handle and utilizing the thumb or forefinger to achieve this.

Figure 5:
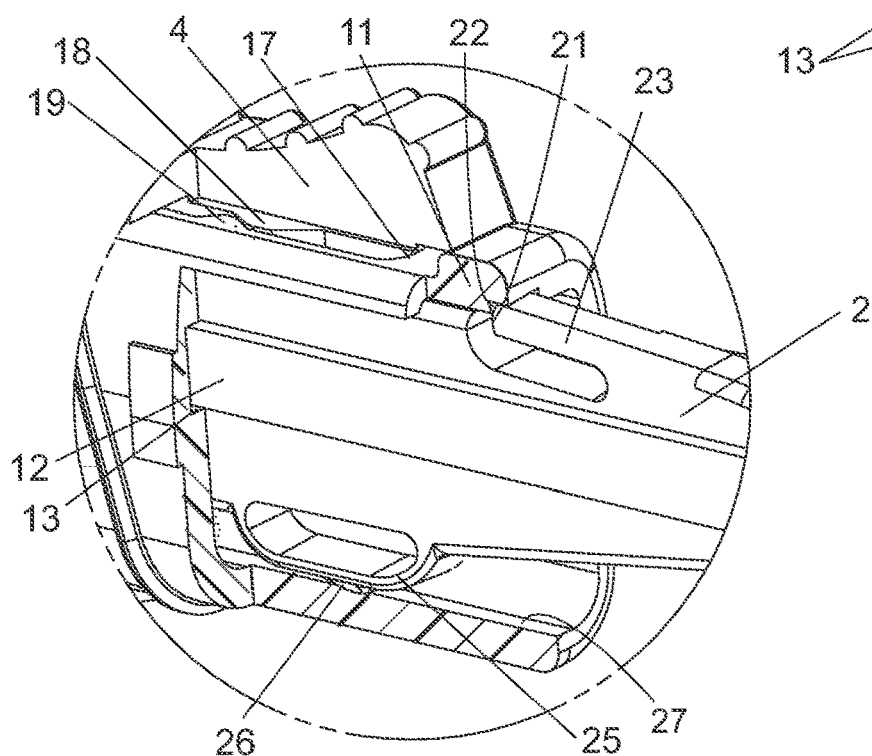
FIG. 5 is a three dimensional version of FIG. 4 showing an existing pair of trapezoidal tooth formations in their inter-engaged positions

The blade carrier with an attached blade and the externally accessible slider is movable from an inoperative condition, in which the blade and blade carrier are retracted within the cavity in the handle, into a fully forward operative position by moving the slider to its fully forward position. In that position, the slider contacts a closed forward end (17) of the slot thus preventing further forward movement. When this position is reached it is accompanied by an audible "click" that signifies the full extent of travel, the "click" being created by a trapezoidal tooth formation (18) on a side of the slider that urges a co-operating tooth formation (19) on the handle slot laterally outwards followed by the co-operating tooth formation snapping back into cooperation with the formation on the slider thus producing the audible "click". These features are shown in FIG. 5.

In the fully forward position, the slider tooth formation is forward of the cooperating handle tooth formation and the handle resilience thus provides a restraining force against rearward movement of the assembly of the blade carrier, blade and slider. With normal use of the scalpel, the slider may be held by the forefinger or between the forefinger and thumb, depending on user preference, or of necessity, as dictated by the procedure. This holding technique, if it is available, provides an additional restraining force for the blade against rearward movement.

Nevertheless, an additional forward lock or restraining feature would be advantageous for procedures requiring a high blade restraining force, especially when the slider cannot be manually restrained. The forward lock or restraining feature, as provided by this invention, activates automatically once a backward bias is applied to the fully extended blade, as would commonly be induced through a stabbing or forward motion action.

Figure 2:
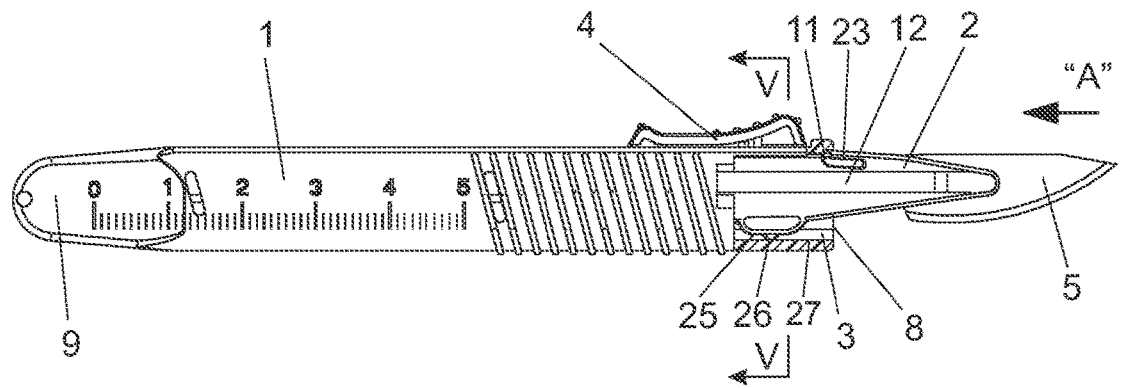
FIG. 2 is a side view of the scalpel illustrated in FIG. 1 showing a portion of the front end of the handle removed.
Figure 3:
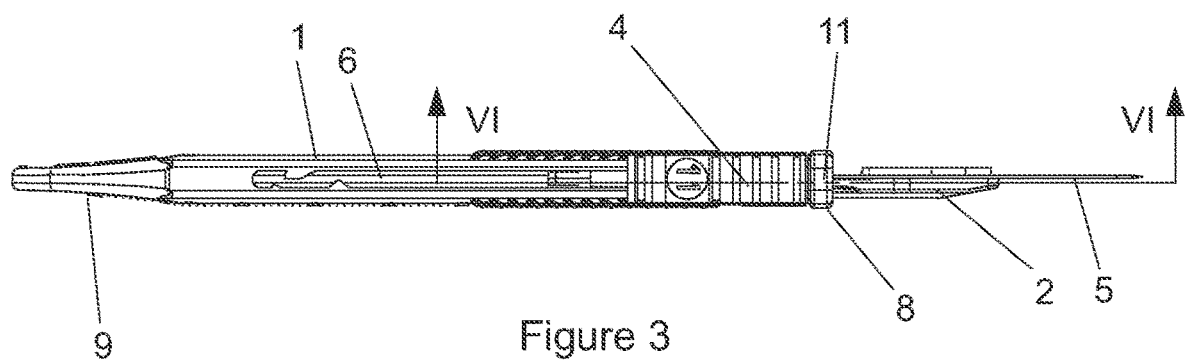
FIG. 3 is a top view of the scalpel.

As provided by this invention, the blade carrier has a catch face (21) directed rearwards in the operative position with the catch face being in at least partial co-operating longitudinal alignment with a co-operating stop face (22) provided on the bridge of the handle such that force exerted on a blade carried by the blade carrier in a direction corresponding to the length of the handle (as indicated by arrow "A" in FIG. 2) causes engagement of the catch face with the stop face to arrest further movement of the blade carrier into the cavity in the handle.

The catch face is formed by an end face of an integral resiliently flexible cantilever pawl formation (23) located on the top of the blade carrier and extending rearwards with the catch face at right angles to the length of the handle. The catch face is inclined upwards and rearwards towards an uppermost rear edge thereof so that the edge has an acute angle. The stop face is shaped complementarily. The cantilever pawl formation has limited flexibility and is arranged to cause the cantilever to flex upwards to promote full engagement of the catch face and stop face as will be quite apparent from FIGS. 8 and 9 once these two surfaces contact each other.

The depth of the stop face will generally depend on the physical properties of the plastic being used for the handle and whilst the catch face may be in total longitudinal alignment with the stop face it is presently considered to be more appropriate to provide a partial co-operating longitudinal alignment with the catch face being laterally movable to create full engagement with the stop face by virtue of it being formed at an end of a somewhat flexible cantilever pawl. Typically, the depth of the stop face in a direction transverse the co-operating guide surfaces could range between 0.2 and 0.4 millimetres and the corresponding size of the catch face is at least equal to that and generally appreciably larger, as illustrated in the drawings.

The extent of a partial co-operating longitudinal alignment of the catch face with the co-operating stop face provided on the handle could generally be within the range of 0.1 to 0.6 millimetres and preferably from 0.3 to 0.5 millimetres, more preferably about 0.45 millimetres. The extent of the partial alignment is shown as "Z" in FIG. 8 and is taken in the direction transverse to the length of the handle.

The co-operating guide surfaces of the keys (12) on each side of the blade carrier and that are received in the cooperating grooves (13) in each side wall of the handle are slightly undersized so that a very limited amount of movement is allowed in a direction at right angles to the length of the grooves in the handle. The blade carrier is biased to a position closer to the top of the handle and one in which the catch face (21) is in partial co-operating longitudinal alignment in the direction of the length of the handle with the co-operating stop face (22) provided on the bridge of the handle, as shown clearly in FIG. 8. The biasing is configured to be overcome by pressure exerted on the slider that corresponds to the force required to retract the blade carrier into the handle so that the catch face and stop face can pass each other during a retraction of the blade into the handle when the normal movements are carried out to effect such retraction.

The biasing of the blade carrier in this embodiment of the invention towards the top of the handle is achieved by an integral leaf spring formation (25) in the form of a squat closed loop at a remote edge of the blade carrier with respect to the slot. The portion of the leaf spring remote from the catch face has a skid formation (26) that slides on a lower surface (27) of the cavity.

Figure 4:
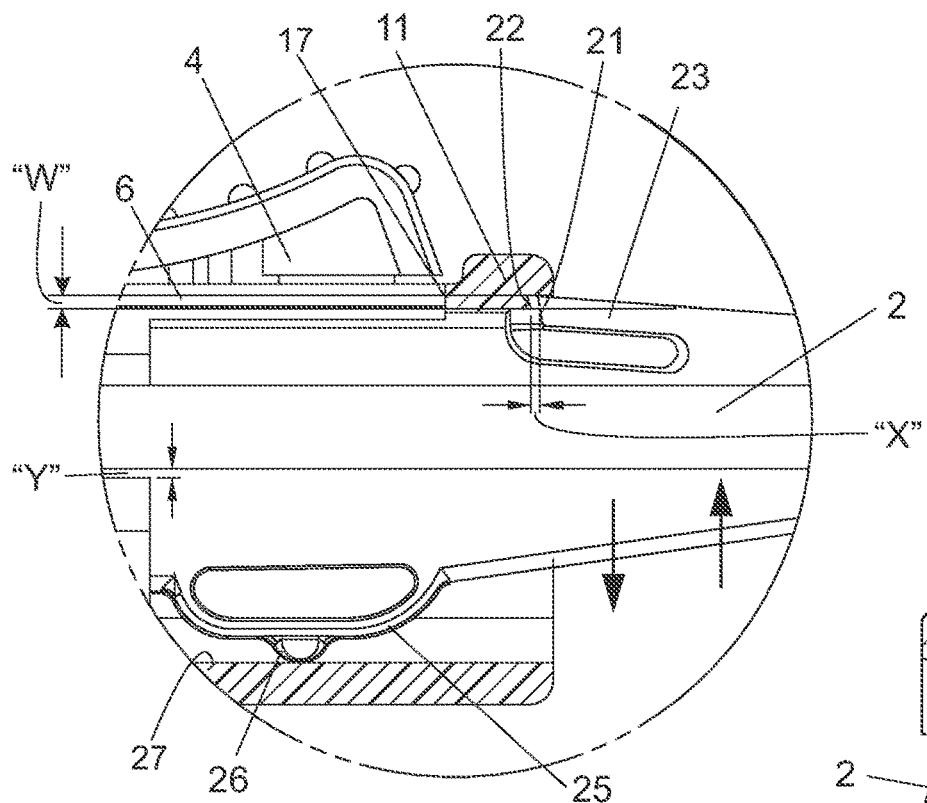
FIG. 4 is a very much enlarged detail of the front end of the handle shown in FIGS. 1 and 2 and showing the spacing of the relevant parts of the scalpel according to the invention.

To further understand the operation of the arrangement of this embodiment of the invention particular reference may be had to FIGS. 4 and 8. When the blade carrier and slider are in the fully forward position, the spring cantilever pawl is positioned facing the stop face within the handle stop recess, with its catch face a minimal distance from the handle stop face. That distance is shown as gap "X" in FIG. 4 and is maintained under normal circumstances by the resilience of the handle that maintains contact of the cooperating inclined surfaces of the trapezoidal tooth formation (18) on a side of the slider that is urged to its terminal position by the co-operating tooth formation (19). Typical dimensions of the gap "X" are from 0.2 to about 0.5 millimetres with a preference towards about 0.3.

As indicated above, the depth of the stop face in a direction transverse the co-operating guide surfaces is indicated by the letter "W" in FIG. 8 and could typically range between 0.1 and 0.7 millimetres, with a preference towards between 0.5 and 0.6 millimetres. It should be noted that an excessive depth "W" could cause excessive flexing of the cantilever pawl, and thereby produce a permanent set in the cantilever pawl. Any permanent distortion of the cantilever pawl could prevent the cantilever pawl from disengaging from the stop face, when the slider is manually pulled backwards.

Movement of the blade carrier transverse to the guide surfaces should be sufficient to ensure a clear passage of the catch face past the stop face when the blade carrier is retracted by normal operation of the slider and could typically range between 0.3 and 0.6 millimetre, with a preference to about 0.5 mm.

In order to ensure proper movement of the catch face into full or partial alignment with the stop face, the normal terminal position of the blade carrier is such that the stop face and catch face are separated by a distance in the direction of the length of the handle of between 0.1 and 0.6 millimetres and preferably between 0.2 and 0.5 millimetres as indicated by the letter "X" in FIG. 4.

Movement of the blade carrier under the influence of the spring is limited by contact of the blade carrier top guide key surface with the handle top guide groove surface. The decreased blade carrier guide key width provides for a clearance between the blade carrier guide key bottom face and the handle guide groove bottom face the extent of which is indicated as gap "Y" in FIG. 4 and which in the present embodiment of the invention is between 0.3 and 0.6 millimetre, with a preference to about 0.5 mm.

When a rearward direction force is applied to the blade, the blade carrier and slider, the spring pawl catch face contacts the inclined stop face of the handle end-stop. The resultant force vector causes the pawl to flex upwards to cause the contact area between the catch face and the stop face to increase to a maximum that is reached when the top edge of the catch face is fully received in the stop recess thus ensuring a positive arresting of the blade carrier assembly.

When the rearward applied force to the blade carrier assembly is relieved, the forward imposed spring loading caused by the interaction of the inclined surfaces of the trapezoidal teeth, causes the gap "X" to be restored. The spring pawl end disengages from the handle stop face as this movement takes place thereby resulting in a deactivation of the forward lock.

By the natural action of pulling the slider rearwards and by reason of the slider profile geometry, a downward force vector is applied to the slider during this procedure. This force vector causes a transverse movement of the blade carrier assembly, under resistance from the blade carrier leaf spring.

The gap between the remote edges of the grooves (gap "Y") is thereby reduced to zero and the blade carrier spring pawl is permitted to pass the handle stop face and thus allow unimpeded. The gap "Y" must clearly be greater than or equal to, preferably greater than, the alignment "Z" of the catch face with the stop face to ensure retraction of the blade carrier assembly. Activation and de-activation is repeatable.

The scalpel offers several improvements and advantages over the prior art. The spring pawl does not engage the handle stop face during normal operation of the blade carrier, whether the blade is being extended from the housing or retracted into the housing, as the pressure applied to the slider to operate the blade carrier ensures that the spring pawl always passes below the handle stop face without engaging it. The spring pawl can be considered to be inert, whether the blade carrier is in the inoperative or operative position, as it only operates or becomes spring loaded once a rearward force is applied to the blade carrier. No unnecessary stresses are thus applied to the spring pawl and a very smooth or natural feel is provided to the operator.

Similarly, the spring pawl never engages the handle stop face unless axial pressure is applied to the blade. This further ensures that there is no weakening or damage caused to the spring pawl through, for example, repeated operation of the blade carrier. Furthermore, no direct pressure is applied to the spring pawl to allow retraction of the blade carrier and blade into the handle. The spring pawl is instead moved through pressure applied to the blade carrier. This not only provides for very smooth operation but also avoids the spring pawl being subjected to forces, particularly bending forces, which could weaken or break it.

Also, the leaf spring is not under tension or pre-load when the blade carrier is in the upwardly biased position, whether the blade carrier is in the retracted condition or in the extended condition. The leaf spring rather ensures that the blade carrier returns to the upwardly biased or rest position after it has moved transversely, under action of pressure applied to the slider. The leaf spring is therefore only tensioned for the duration of the forward or rearward travel of the blade carrier. This ensures that leaf spring does not suffer weakening or permanent set through continuous loading.

A further advantage of the scalpel is that the forward lock cannot be inadvertently deactivated by pulling back on the slider while performing a stabbing action. Any rearward assistance afforded the slider during a stabbing procedure while the forward lock is engaged would only assist blade restraint. As soon as the blade encounters axial resistance it moves the blade carrier rearwards so that the catch face of the spring pawl engages with the stop face and is unable to be disengaged by downward and rearward motion. Only releasing the axially rearward force on the blade and allowing the catch face of the spring pawl to move forward and disengage with, and move away from, the stop face will permit disengagement of the front lock or restraint and allow retraction of the blade and blade carrier into the handle.

It will be understood that numerous variations may be made to the embodiment of the invention described above without departing from the scope hereof. For example, the catch face could be provided on the slider instead of on the blade carrier. Also, it should be noted that application of the invention is not restricted to the type of retractable scalpel described above and it could be applicable to numerous other designs, shapes and configurations of scalpel. Also, the dimensions given above for the various gaps and spaces are purely indicative of proportion and are not to be interpreted as being limiting on the scope of the invention.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A scalpel comprising:
a handle with a longitudinally extending cavity therein;
a blade carrier within the cavity and movable longitudinally relative to the handle between an operative position in which a blade carried by the blade carrier is exposed for use at an open end of the cavity and an inoperative position in which the blade carried thereby is retracted within the cavity in the handle, the blade carrier having a top edge; and
a manually operable slider associated with the blade carrier and passing through a slot in a wall of the handle at a top edge of the handle defining the cavity,
wherein the blade carrier is confined to longitudinal movement within the cavity by longitudinally extending co-operating guide surfaces,
wherein the blade carrier has a catch face directed rearwards in the operative position with the catch face being in at least partial co-operating alignment with a co-operating stop face provided on the handle in the normal operative position of the blade carrier such that force exerted on the blade carried by the blade carrier in a direction corresponding to a length of the handle causes engagement of the catch face with the stop face to arrest movement of the blade carrier into the cavity in the handle,
wherein the co-operating guide surfaces are configured to allow limited transverse movement of the guide surfaces relative to each other and are biased to a position in which the catch face is in the at least partial co-operating alignment with the co-operating stop face provided on the handle with the biasing being configured to be overcome by pressure exerted on the slider that corresponds to pressure required to retract the blade carrier into the handle so that the catch face and stop face can pass each other during a retraction of the blade into the handle consequent on a transverse movement of the guide surfaces relative to each other, and
wherein the catch face protrudes from the top edge of the blade carrier by a first distance and the configuration of the co-operating guide surfaces is such that the allowed transverse movement of the guide surfaces relative to each other exceeds the first distance, thereby to allow a clear passage of the catch face past the stop face when the blade carrier is retracted by operation of the slider.

2. The scalpel as claimed in claim 1 in which the catch face is defined by an end face of an integral resiliently flexible cantilever pawl formation located on a top of the blade carrier and extending rearwards with the catch face transverse to the handle.

3. The scalpel as claimed in claim 2 in which the catch face is inclined upwards and rearwards towards a rear edge of the cantilever pawl formation and the stop face is shaped complimentary and is arranged to cause the cantilever pawl formation to flex upwards to promote full engagement of the catch face and the stop face.

4. The scalpel as claimed in claim 1 in which the stop face is formed in an integral bridge at the front end of the top edge of the handle where it has an endless loop formation surrounding an open end to the cavity.

5. The scalpel as claimed in claim 1 in which the longitudinally extending co-operating guide surfaces include at least one pair of cooperating guide keys and grooves, a first one of the pairs comprising a longitudinally extending guide key or groove on a first side of the blade carrier co-operating with a longitudinally extending groove or key, respectively, on a first inner surface of the cavity such that the cooperating keys and grooves guide the blade carrier for longitudinal movement along the handle in which instance the groove of the first pair, whether it be on the blade carrier or on the inner surface of the cavity, is slightly wider than the respective key with which it cooperates, to provide for movement of the blade carrier away from the top of the handle to enable the catch face to pass the stop face during retraction of the blade into the handle by pressure exerted on the slider.

6. The scalpel as claimed in claim 5, wherein the at least one pair of cooperating guide keys and grooves further comprises a second pair of cooperating keys and grooves including a longitudinally extending guide key or groove on a second side of the blade carrier cooperating with a longitudinally extending groove or key, respectively, on a second inner surface of the cavity, such that a key or groove is provided on each of two opposite sides of the blade carrier with a co-operating groove or key, respectively, in each of two opposite sides of the cavity.

7. The scalpel as claimed in claim 1 in which biasing of the blade carrier towards the top of the handle is achieved by an integral leaf spring formation in sliding relationship relative to a lower surface of the cavity.

8. The scalpel as claimed in claim 7 in which the integral leaf spring formation is in the form of a squat closed loop at an edge of the blade carrier remote from the catch face.

9. The scalpel as claimed in either one of claim 7 or 8 in which the integral leaf spring formation has a skid formation carried thereby for contacting a co-operating surface of the cavity.

10. The scalpel as claimed in claim 1 in which the extent of the at least partial co-operating alignment of the catch face with the co-operating stop face provided on the handle is within the range of 0.1 and 0.6 millimeters.

11. The scalpel as claimed in claim 1 in which the depth of the stop face in a direction transverse the co-operating guide surfaces is within the range of 0.1 and 0.7 millimeters.

12. The scalpel as claimed in claim 1 in which the handle is molded as a single piece molding with an integral bridge defining an endless loop formation surrounding an open end to the cavity through which the blade carrier may be introduced into the cavity and wherein the slider is separately formed and snap fitted to the blade carrier after introduction thereof through the open end of the cavity to form a blade carrier and slider assembly with a part of the slider passing through a slot along the top of the handle.

13. The scalpel as claimed in claim 1 wherein the catch face engaging with the stop face prevents any further movement of the blade carrier into the cavity of the handle.

* * * * *